Figure 1:
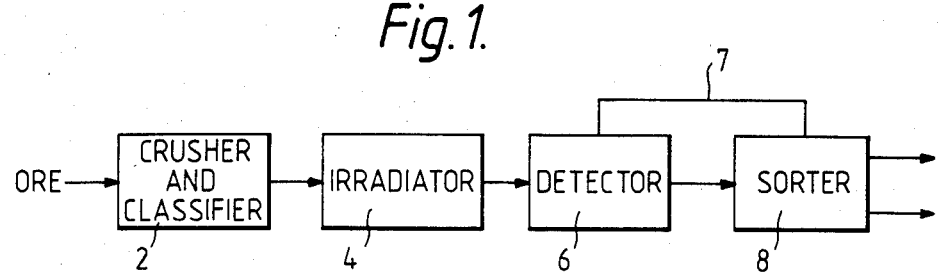

United States Patent [19]

Clayton et al.

[11] Patent Number: 4,696,782
[45] Date of Patent: Sep. 29, 1987

[54] ORE IRRADIATOR

[75] Inventors: Colin G. Clayton, Abingdon; Ramon Spackman, Didcot, both of England

[73] Assignee: United Kingdom Atomic Energy Authority, London, England

[21] Appl. No.: 674,738

[22] Filed: Nov. 26, 1984

[30] Foreign Application Priority Data

Nov. 30, 1983 [GB] United Kingdom ............. 8331911

[51] Int. Cl.$^4$ ............................................. G21G 1/06
[52] U.S. Cl. ................................... 376/159; 376/117; 376/202; 376/151; 376/194; 313/361.1; 222/199
[58] Field of Search ............... 376/127, 129, 130, 144, 376/145, 202, 114–117, 108–110, 157, 159, 151, 194; 250/390 I, 496.1, 492.1–492.3, 493.1; 328/233; 313/361.1, 359.1, 231.41; 222/199

[56] References Cited

U.S. PATENT DOCUMENTS

| | | | |
|---|---|---|---|
| 2,576,600 | 11/1951 | Hanson | 376/194 |
| 2,929,933 | 3/1960 | Ela, Jr. et al. | 376/192 |
| 3,551,728 | 12/1970 | Croitoru | 328/233 |
| 3,860,827 | 1/1975 | Cranberg | 376/151 |
| 3,971,493 | 7/1976 | Williams | 222/199 |
| 3,974,391 | 8/1976 | Offermann | 250/492.3 |
| 4,071,170 | 1/1978 | Gunzel et al. | 222/199 |
| 4,298,804 | 11/1981 | Colditz | 376/151 |

FOREIGN PATENT DOCUMENTS

| | | | |
|---|---|---|---|
| 0059033 | 9/1982 | European Pat. Off. | 376/159 |
| 848720 | 9/1952 | Fed. Rep. of Germany | 222/199 |
| 1243262 | 8/1971 | United Kingdom | 376/151 |
| 2055465 | 3/1981 | United Kingdom | 376/159 |
| 2101304 | 1/1983 | United Kingdom . | |

OTHER PUBLICATIONS

Kerntechnik, vol. 17, No. 1, 1975, pp. 36–41, Schraub.
Nuclear Instruments & Methods, vol. 89, No. 1, 1970, pp. 167–172, Jungerman et al.

Primary Examiner—Harvey E. Behrend
Attorney, Agent, or Firm—William R. Hinds

[57] ABSTRACT

An irradiator for irradiating lumps of ore, to activate a selected substance in the ore by neutron activation, consists of a cylindrical chamber 10, a vibrated conical base 20 to control passage of the lumps through the chamber 10, and at least one coaxial annular neutron source 30 at one end of the chamber 10. The neutron source 30 is arranged so that all the lumps of ore are activated uniformly.

10 Claims, 2 Drawing Figures

ORE IRRADIATOR

This invention relates to apparatus for detecting the presence of a selected substance in ores by neutron activation analysis, for example the gold content of gold-bearing ores.

A practical gold ore sorting plant needs to be able to process several tens of tonnes of ore an hour, and hence must use a rapid analytical technique. A suitable technique is neutron activation analysis using the reaction $^{197}$Au (n, n' $\gamma$) $^{197m}$Au to activate gold present in a lump of ore, the $^{197m}$Au nuclides so produced decaying with a half-life of about 7.8 seconds, with the emission of $\gamma$-rays of energy 279 keV. British Patent Specifications Nos. 2 055 465B and 2 101 304B (U.S. Pat. No. 4,340,443, and U.S. Ser. No. 383,686 filed 27 May 1982, respectively) which are incorporated by reference herein, describe apparatus for sorting gold bearing ores in which lumps of ore are activated by the above reaction, the $\gamma$-rays emitted subsequently being detected and analysed to assess the gold content of the ores.

According to the present invention there is provided an irradiator for irradiating lumps of ore for detecting the presence of a selected substance in the lumps, the irradiator comprising a cylindrical chamber, means for causing the lumps to pass through the chamber, and adjacent to one end of the chamber at least one coaxial annular neutron source arranged so that the resulting neutron flux in the chamber ensures that in passing through the chamber all the lumps are activated uniformly, that is to say that every lump of the same gold grade (mass of gold/mass of ore) has the same specific activity (mass of $^{197m}$Au nuclei/mass of gold) to an accuracy of about $\pm 5\%$.

Preferably the chamber is defined by an upwardly extending cylindrical wall and a coaxial conical sloping base defining an opening between the bottom of the wall and the base, and the base may be movable axially with respect to the wall to control the passage of the lumps through the chamber and out of the opening.

In a preferred embodiment there is provided a coaxial circular target onto which a beam of accelerated ions is arranged to be incident to generate the neutrons, the beam being scanned over at least one annular path on the target.

In an embodiment of the invention for detecting the presence of gold in gold-bearing ores, each neutron source comprises a lithium target arranged to be bombarded by a beam of high energy protons so as to produce neutrons of energy between 0.5 and 3.0 MeV.

The invention also provides an ore sorting apparatus including the irradiator described above.

Figure 2:
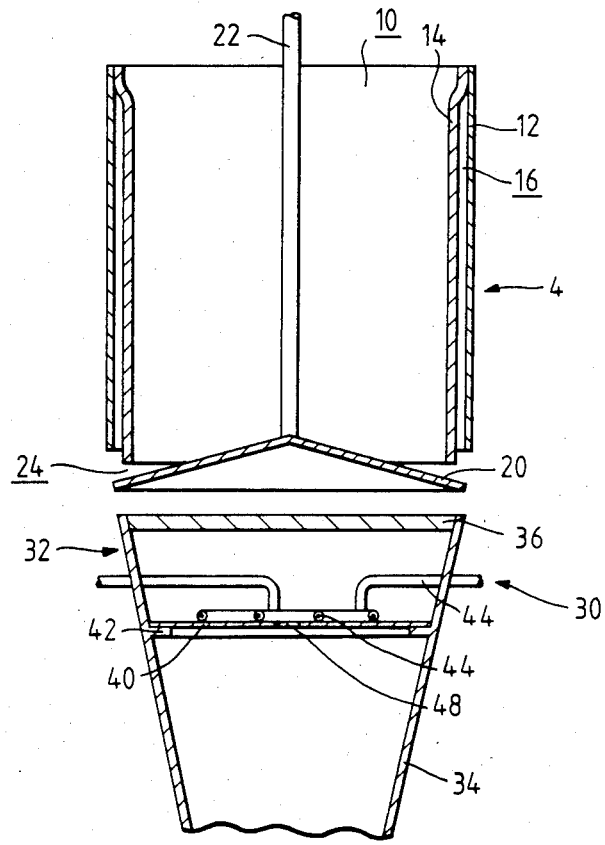

The invention will now be further described by way of example only and with reference to the accompanying drawings, in which:

FIG. 1 is a flow diagram of a gold ore sorting apparatus including an irradiator according to the invention; and FIG. 2 is a cross-sectional representation of the irradiator of FIG. 1.

Referring to FIG. 1, a gold ore sorting apparatus comprises a rock crusher and classifier 2 to which mined ore is supplied, in which the ore is crushed into lumps and from which emerges a stream of lumps corresponding to mesh size of about 75 mm, while lumps smaller than mesh size about 35 mm rejected. The stream of lumps is passed through an irradiator 4 to be described in more detail later, and then all the lumps are caused to pass a $\gamma$-ray detector assembly 6 arranged to detect $\gamma$-rays having an energy of 279 keV arising from the decay of $^{197m}$Au nuclides and so signifying the presence of gold in the lumps of ore. Each lump of ore is interrogated individually by the detector assembly 6 to establish whether its gold content lies above or below some predetermined concentration. The critical concentration is typically in the range 0.5 to 5 parts per million (ppm), and might for example be set at 1 ppm. Each lump of ore is then passed into a sorter 8 arranged by means of a cable 7 to respond to signals from the detector assembly 6, and to sort each lump of ore into one of two outlet streams depending on whether the gold concentration in the lump lies above or below the predetermined concentration.

The crusher and classifier 2 and the sorter 8 may be of types well known in the art, while the detector assembly 6 may be as described more fully in the aforementioned specifications to which reference may be made, the crusher and classifier 2, the sorter 8 and the detector assembly 6 not being the subject of the invention.

Referring to FIG. 2, the irradiator 4 comprises an irradiation chamber 10 of diameter 520 mm defined by an upright hollow open-ended cylinder 12 about 1 mm thick made of a carbon fibre reinforced plastics material, with a wear-resistant lining 14 of polyurethane about 3.5 mm thick bonded at its upper end to the cylinder 12, there being a gap 16 about 3 mm wide between the unbonded portion of the lining 14 and the cylinder 12. The lining 14 extends a short distance below the bottom of the cylinder 12. The base of the chamber 10 is defined by a conical base plate 20, also made of carbon fibre reinforced plastics material coated with wear-resistant steel on its upper surface. The base plate 20 is supported by a shaft 22 so as to provide a gap 24 between the edge of the base plate 20 and the bottom edge of the lining 14, of width about 80 mm.

Directly beneath the base plate 20 is a neutron source 30 comprising a target 32 at the end of an evacuated beam tube 34. The target 32 comprises a palladium end plate 36 closing the end of the beam tube 34, and a circular lithium foil 40 about 0.3 mm thick supported within the beam tube 34 by an internal circumferential flange 42 and by a number of tubes 44 (only two are shown), each tube 44 supporting the foil 40 along a respective annular path and having end portions extending radially to pass through the wall of the beam tube 34. A central hole 48 through the foil 40 ensures equality of pressure on the two sides thereof.

In operation of the irradiator 4, lumps of ore are fed into the chamber 10 from above, while the base plate 20 is vibrated vertically at 50 Hz with an amplitude of about ½ mm by means of the shaft 22, to control the passage of the lumps through the chamber 10 and out from the gap 24. A beam of protons is accelerated along the beam tube 34 so that the protons of energy 4.5 MeV are incident on the lithium foil 40, and coolant water is passed through the tubes 44 to ensure the temperature of the foil 40 does not reach its melting point, 186° C. The proton beam, of width about 20 mm, is scanned over three concentric annular paths on the foil 40, the paths lying between the annular portions of adjacent tubes 44, and having mean radii 230 mm, 190 mm and 50 mm, and the times spent on those paths being in the ratio 2:10:3.

A flux of fast neutrons is produced by the reaction $_3^7$Li (p, n) $_4^7$Be, with an energy range from 0.6 MeV to 2.8 MeV, this range being determined by the thickness of the foil 40 and the energy of the incident protons and being chosen to lie near the maximum cross-section for activation of gold nuclei, Au$^{197}$. Those protons which do not undergo this reaction with lithium emerge from the foil 40 with an energy of about 3.3 MeV and are incident on the end plate 36, in which their energy is dissipated as heat.

The fast neutrons pass through the end plate 36 and the base plate 20 to irradiate the lumps of ore passing through the irradiation chamber 10. If any gold is present in a lump of ore it will be activated by the reaction $^{197m}$Au (n, n' $\gamma$) $^{197m}$Au the cross-section for which is a maximum for neutrons of energy about 2.5 MeV. Fast neutrons of energy between about 0.6 MeV and 2.8 MeV are capable of bringing about this activation, but have insufficient energy to bring about activation by (n, p) reactions of other elements which are likely to be present in the ore, such as aluminium and silicon. The annular paths over which the proton beam is scanned over the foil 40 produce a neutron flux within the chamber 10 such that all the lumps are activated substantially uniformly, however they may pass through the chamber 10. In an alternative mode of operation, the proton beam is scanned over a single annular path of mean radius 230 mm, which again provides substantially uniform activation of the lumps.

Although the cylinder 12 has been described as being made of carbon fibre reinforced plastics material, it will be appreciated that it might alternatively be made of other materials, for example a titanium alloy and the lining 14 might be dispensed with. The wall of the chamber 10 must be strong enough to contain the lumps of ore, and be adequately wear-resistant. Furthermore it is preferably thin and with low inelastic and elastic cross-section for neutron scattering, in order to minimize the reflection of neutrons of energy below about 0.6 MeV back into the chamber 10. The effective threshold energy for the gold activation reaction utilised is 0.6 MeV. Neutrons of energy lower than that are capable of bringing about excitation by (n, $\gamma$) reactions of other elements present in the ore, and hence are undesirable.

It will also be understood that the neutron source 30 might be replaced by a source comprising a layer about 0.3 mm thick of lithium coated onto a suitable support plate, such as niobium, over which a proton beam is scanned, the support plate defining ducts for a coolant fluid. Niobium is particularly suitable as it does not form an alloy layer at the lithium/niobium interface, so that the thickness of the lithium layer and consequently the energy of the neutrons are well defined. Furthermore, at the operating temperature (below 186° C.), hydrogen atoms (i.e. protons which have slowed down) diffuse sufficiently rapidly through the niobium plate that there is no tendency for hydrogen to accumulate at the interface to form bubbles. Alternative neutron sources such as those utilizing a D (D, n) $^3$He reaction may be used as long as the neutrons produced are of energies less than about 3 MeV.

We claim:

1. An irradiator for irradiating lumps of ore for detecting the presence of a selected substance in the lumps, the irradiator comprising a cylindrical chamber, means for causing the lumps to pass through the chamber, and adjacent to but outside one end of the chamber at least one coaxial annular neutron source arranged so that the resulting neutron flux in the chamber ensures that in passing through the chamber all the lumps are activated uniformly each such neutron source comprising a target which generates neutrons when a beam of ions is incident upon it, the irradiator also including means for generating a beam of ions and for directing said beam of ions onto said target in an annular pattern, said pattern being coaxial with said chamber.

2. An irradiator as claimed in claim 1 wherein the chamber is defined by an upwardly extending cylindrical wall and a coaxial conical sloping base defining an opening between the bottom of the wall and the base, and the base is movable axially with respect to the wall to control the passage of the lumps through the chamber and out of the opening.

3. An irradiator as claimed in claim 1 wherein the means for directing said beam of ions onto said target in an annular pattern includes means for scanning said beam of ions wherein each such neutron source comprises a target over at least one coaxial annular path on said target.

4. An irradiator as claimed in claim 3 wherein the scanning means is arranged to scan the beam over three concentric annular paths on the target.

5. An irradiator as claimed in claim 3 for detecting the presence of gold in gold-bearing ores, wherein the target comprises lithium, and the beam generating means generates a beam of high energy protons so as to produce neutrons of energy between 0.5 and 3.0 MeV.

6. An irradiator as claimed in claim 5 wherein the irradiator includes an evacuatable chamber, and means for evacuating the evacuatable chamber, and the target comprises a relatively thin foil of lithium supported by a support structure whereby the foil is supported within the evacuatable chamber to be bombarded by the proton beam, the support structure including a pipe for the passage of a coolant fluid and having at least one annular gap therethrough such that a portion of the foil bridges the gap and is exposed to equal pressures on both sides thereof, the proton beam being scanned over the portion of the foil which bridges the gap.

7. An irradiator as claimed in claim 5 wherein the target comprises a relatively thin layer of lithium coated onto one side of a backing plate of niobium which does not form an alloy layer at the interface, and through which, in operation, hydrogen diffuses at such a rate that bubbles do not form at the interface.

8. An irradiator as claimed in claim 1 wherein the cylindrical chamber is defined in part by a cylindrical lining of a flexible, wear-resistant, plastics material supported within a cylindrical wall of a relatively rigid plastics material.

9. An irradiator as claimed in claim 8 wherein the lining is spaced inwardly from the wall over at least part of its length.

10. An ore sorting apparatus including an irradiator as claimed in claim 1.

* * * * *